United States Patent [19]
Harden

[11] Patent Number: 5,948,502
[45] Date of Patent: Sep. 7, 1999

[54] TANNING SYSTEMS

[76] Inventor: Glen Raymond Harden, The Warren, Whybornes Chase, Minster, Kent, Sheerness ME12 2H2, United Kingdom

[21] Appl. No.: 08/960,891

[22] Filed: Oct. 30, 1997

[30]    Foreign Application Priority Data

Nov. 22, 1996 [GB] United Kingdom .................... 9624372

[51] Int. Cl.⁶ ....................................................... B32B 3/00
[52] U.S. Cl. ............................. 428/99; 40/586; 132/319; 132/333; 428/42.1; 428/203; 428/204; 428/914
[58] Field of Search ............................... 428/99, 42.1, 38, 428/914, 203, 204; 40/586; 132/319, 333

[56]                References Cited

U.S. PATENT DOCUMENTS

| 2,851,805 | 9/1958 | Allen ........................................ 132/319 |
| 4,302,263 | 11/1981 | Postupack ................................. 428/31 |
| 4,358,488 | 11/1982 | Dunklin ..................................... 428/31 |
| 4,594,276 | 6/1986 | Relyea ..................................... 428/42.1 |
| 4,753,239 | 6/1988 | Vitolo ....................................... 128/372 |
| 5,353,453 | 10/1994 | Naumann ..................................... 5/417 |

FOREIGN PATENT DOCUMENTS 0267655  5/1988  European Pat. Off. .

*Primary Examiner*—Nasser Ahmad
*Attorney, Agent, or Firm*—Bachman & LaPointe, P.C.

[57]              ABSTRACT

An improved tanning system involves the use of a film of material which is permeable to ultra-violet light and which is adapted to be laid on part of a human body, for example the torso. The film is covered in certain desired regions with a material which is impermeable to ultra-violet light which regions are surrounded by regions which are only slightly permeable to ultra-violet light. When a person wearing the film is subjected to tanning, the result is improved appearance of the torso, for example, the person may look fitter, slimmer and/or more muscular. The tanning may be achieved by either natural sunlight or by means of a sunbed.

6 Claims, 2 Drawing Sheets

TANNING SYSTEMS

FIELD OF THE INVENTION

This invention relates to improved techniques for tanning the skin.

SUMMARY OF THE INVENTION

According to the invention, there is provided a film of material which is permeable to ultra-violet light and which is adapted to be laid on a part of the human body, wherein the film is covered in certain desired regions with a material which is impermeable to ultra-violet light.

The impermeable regions are desirably surrounded by regions which are only slightly permeable to ultra-violet light. The latter regions may be graded between the impermeable regions and the remainder of the film whereby permeability is increased with increasing distance from the impermeable regions.

Preferably, the film is adapted to be fitted to a human torso and the impermeable regions are so arranged as to improve the appearance of a body which is subjected to tanning either by natural sunlight or by a sunbed. The film may be provided with fastening tapes or other suitable fastening means for this purpose. The film may have the shape of either a male or a female torso. Alternatively, the film may be adapted to be fitted to a human face or limb.

The film is desirably made of a transparent plastics material.

BRIEF DESCRIPTION OF THE DRAWINGS

The invention will now be described in detail, by way of example, with reference to the drawings, in which.

DESCRIPTION OF PREFERRED EMBODIMENT

Figure 1:
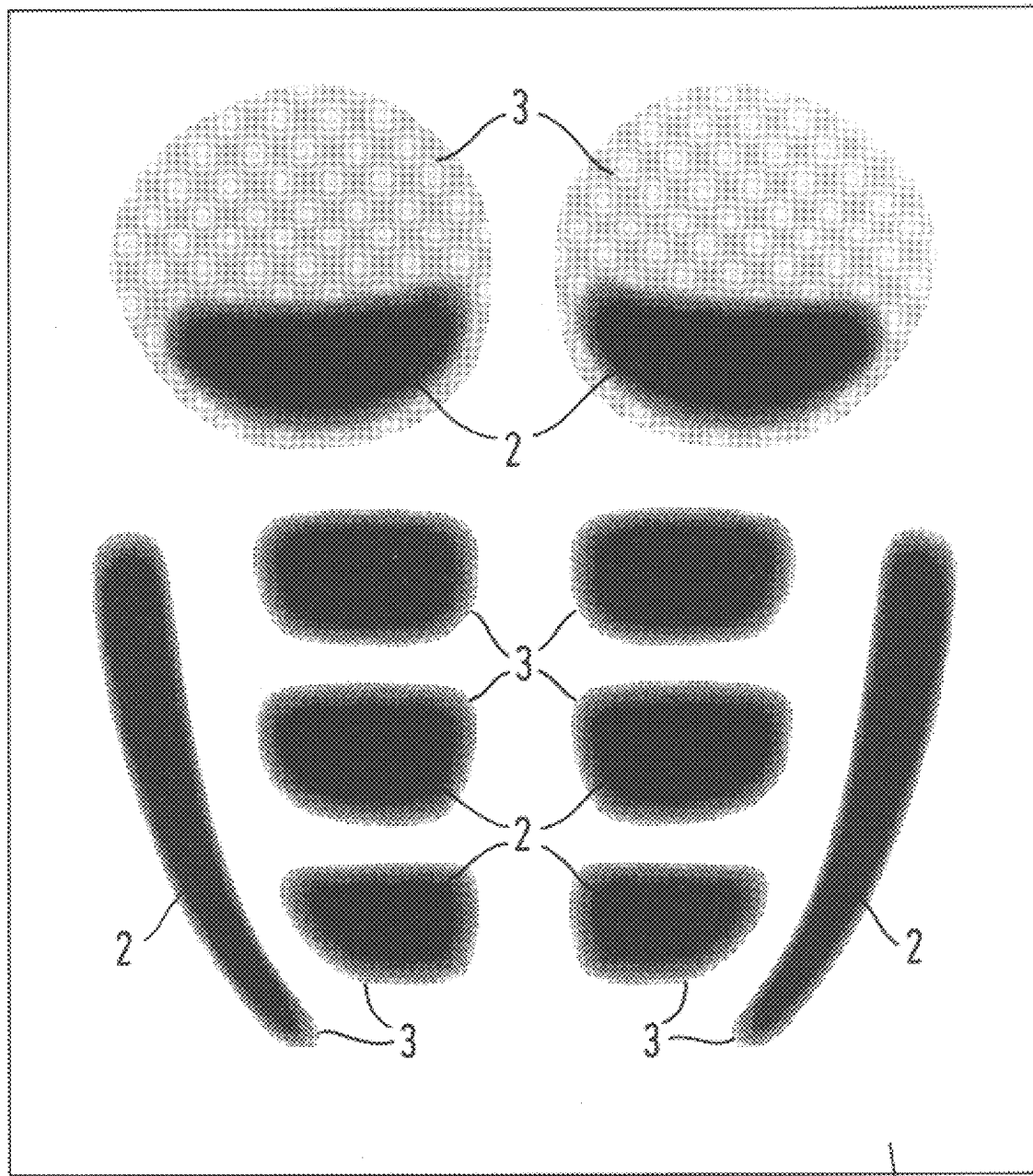
FIG. 1 is an illustration of one embodiment of a film according to the invention.

Referring to the drawings, a film 1 according to the invention is coated with regions 2 of a material which is impermeable to ultra-violet light and further regions 3 which are only partially permeable to ultra-violet light.

Figure 2:
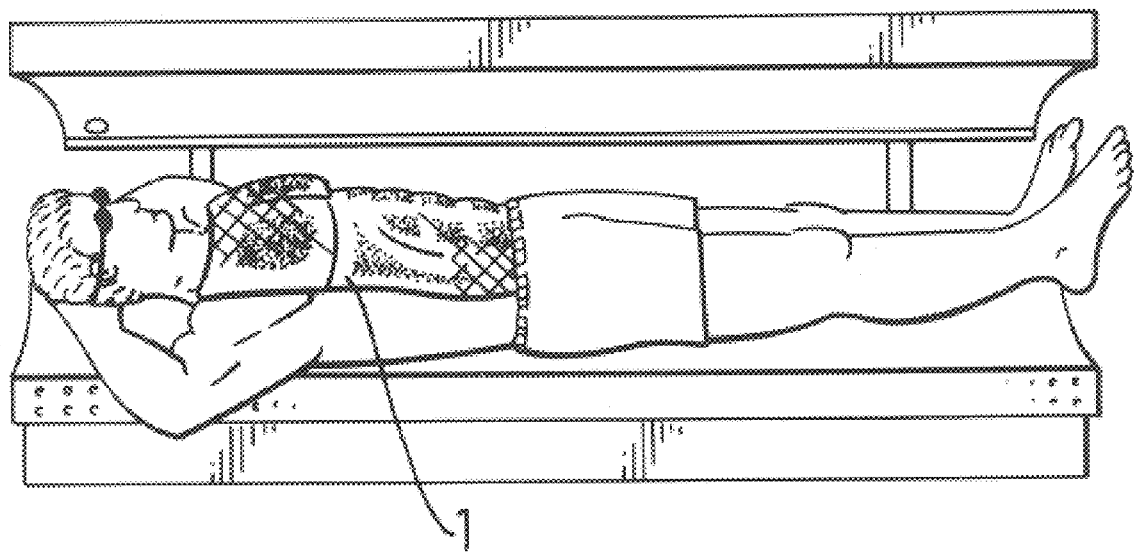
FIG. 2 shows the film illustrated in FIG. 1 applied to a human torso in a sunbed.
Figure 3:
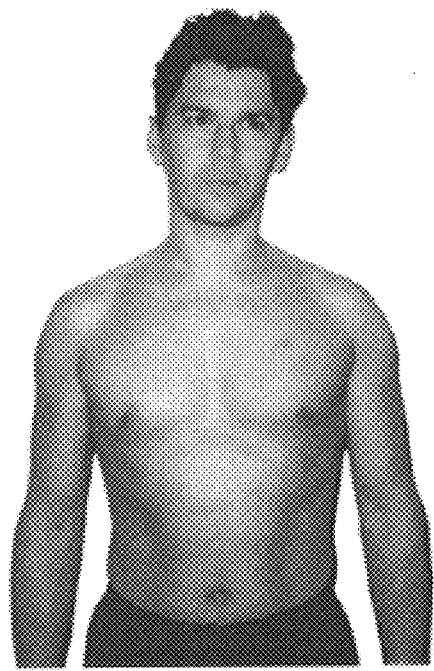
FIG. 3 shows a person before being subjected to tanning.
Figure 4:
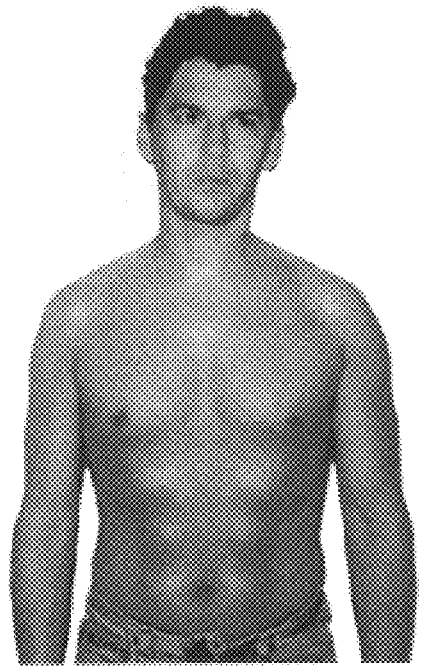
FIG. 4 shows the same person as shown in FIG. 3 but after being subjected to tanning with the film shown in FIGS. 1 and 2 in place during the tanning.

In use, the film is laid onto the front of a human torso and the individual concerned then subjects himself to tanning either by natural sunlight or in a sunbed as shown in FIG. 2 of the drawings. It has been found that, after a comparatively short period of time, the appearance of the body can be dramatically improved making the subject look fitter, slimmer and more muscular as is illustrated by FIGS. 3 and 4 of the drawings which show the same person before and after tanning with a film according to the invention.

The invention is not restricted to use by males but could also be used by females although in that case the impermeable regions will be altered in order to give the female torso a flattering appearance after tanning. The film could also be used on other parts of the body, for example the limbs or the face, for example to highlight cheekbones in order to give a slimmer look to the face.

I claim:

1. A film of material which comprises a human body tanning film which is permeable to ultra-violet light and which has a shape suitable to be laid on part of a human body, wherein the film is covered in certain desired regions with a material which is impermeable to ultra-violet light and wherein said impermeable regions are surrounded by further regions which are graded between said impermeable regions and the remainder of the film whereby permeability is increased with increasing distance from the said impermeable regions.

2. A film as claimed in claim 1, in which the film has a shape suitable to be fitted to a human torso.

3. A film as claimed in claim 2, in which the film is provided with fastening tapes.

4. A film as claimed in claim 1, in which the film has a shape suitable to be fitted to a human face.

5. A film as claimed in claim 1, in which the film has a shape suitable to be fitted to a human limb.

6. A film as claimed in claim 1, in which the film is made of a transparent plastics material.

* * * * *